US007886748B2

(12) United States Patent
Boxer Wachler

(10) Patent No.: US 7,886,748 B2
(45) Date of Patent: Feb. 15, 2011

(54) METHOD FOR USING INTENSE PULSED LIGHT TO NON-INVASIVELY TREAT CONJUNCTIVAL BLOOD VESSELS, PIGMENTED LESIONS, AND OTHER PROBLEMS

(75) Inventor: Brian S. Boxer Wachler, Santa Monica, CA (US)

(73) Assignee: Advanced Vision Education, LLC, Beverly Hills, CA (US)

(*) Notice: Subject to any disclaimer, the term of this patent is extended or adjusted under 35 U.S.C. 154(b) by 1328 days.

(21) Appl. No.: 11/357,577

(22) Filed: Feb. 15, 2006

(65) Prior Publication Data

US 2007/0191821 A1 Aug. 16, 2007

(51) Int. Cl.
*A61B 19/00* (2006.01)
(52) U.S. Cl. .......................................... 128/898; 607/88
(58) Field of Classification Search .................. 606/2, 606/9, 11, 20, 107, 4, 6; 128/898; 607/89, 607/88
See application file for complete search history.

(56) References Cited

U.S. PATENT DOCUMENTS

| | | | | |
|---|---|---|---|---|
| 5,672,172 A | * | 9/1997 | Zupkas | 606/20 |
| 6,676,655 B2 | * | 1/2004 | McDaniel | 606/9 |
| 6,723,090 B2 | * | 4/2004 | Altshuler et al. | 606/9 |
| 6,733,493 B2 | * | 5/2004 | Gruzdev et al. | 606/9 |
| 6,746,444 B2 | * | 6/2004 | Key | 606/9 |
| 2004/0167499 A1 | * | 8/2004 | Grove et al. | 606/9 |
| 2004/0167502 A1 | * | 8/2004 | Weckwerth et al. | 606/9 |
| 2005/0177141 A1 | * | 8/2005 | Davenport et al. | 606/9 |
| 2005/0215987 A1 | * | 9/2005 | Slatkine | 606/9 |

OTHER PUBLICATIONS

Description of Quadra Q4 Platinum Series Intense Pulsed Light, http://www.quadraq4.com, 2000.
Intense Pulsed Light™ and Laser Technology Brochure.
IPL™ Quantum SR Operator's Manuel, Oct. 2002.
Sutter, et al., Abstract of *Ocular complications of PhotoDerm VL therapy for facial port-wine stain*, http://www.ncbi.nlm.nih.gov, Jun. 2004.
Sadick, *Update on Non-Ablative Light Therapy For Rejuvenation: A Review*, Lasers in Surgery and Medicine 32: 2003, pp. 120-128.
Raulin, *IPL Technology: A Review*, Lasers in Surgery and Medicine 32: 2003, pp. 78-87.
Toyos, et al., *Case report: Dry-eye symptoms improve with intense pulsed light treatment*, EyeWorld, Sep. 2005, pp. 73-75.

* cited by examiner

*Primary Examiner*—Ahmed M Farah
(74) *Attorney, Agent, or Firm*—Samuel L. Alberstadt

(57) ABSTRACT

A new configuration of intense pulsed light (IPL) equipment includes a handpiece that allows the application of IPL directly to the eye and eyelid. The handpiece is sized and configured for precise digital manipulation. The invention also includes a distance guide for maintaining precise distances between the area to be treated and a crystal mounted in the handpiece. Eye shields protect the cornea and surrounding sclera during application of IPL.

5 Claims, 3 Drawing Sheets

METHOD FOR USING INTENSE PULSED LIGHT TO NON-INVASIVELY TREAT CONJUNCTIVAL BLOOD VESSELS, PIGMENTED LESIONS, AND OTHER PROBLEMS

FIELD OF THE INVENTION

This invention relates to an apparatus and method for treating the eye and eyelid with intense pulsed light (IPL).

BACKGROUND OF THE INVENTION

Superficial blood vessels of the conjunctiva that overlie the sclera are a cosmetic source of dissatisfaction among millions of people. These blood vessels vary in size, length, and number. Often such blood vessels are unsightly and lead to diminished self-esteem or even social stigma. People with large numbers of such vessels may appear tired or fatigued to others, affecting the perception of co-workers, supervisors, family, and friends. Therefore, people with such blood vessels may desire whiter appearing eyes for improved cosmesis. Currently there is no permanent treatment for such problems.

Lasers are used for the targeted treatment of hemoglobin in blood vessels, but lasers can easily penetrate through the sclera and are dangerous to inner ocular structures such as the choroids and retina. Surgical vein stripping in theory is possible, but it is not performed due to the invasiveness of the procedure. Temporary treatments exist for conjunctival blood vessels in the form of pharmaceutical eye drops that contain vasoconstrictive agents. However, these agents typically last 3-6 hours and require reapplication. When such medicated drops are discontinued, the rebound effect can lead to worsening of conjunctival injection and vascular engorgement. The widespread use of such topical eye drops reflects the need for a permanent solution to this widespread problem. A similar problem exists with superficial lesions of the conjunctiva, such as brown nevi, yellow pinguecula, pigmented tumors, and other structures that can be cosmetically unattractive. The only permanent treatment is invasive surgical removal.

Blepharitis is a common condition of the eyelids that causes ocular discomfort and may lead to dry eyes, corneal scarring, and loss of vision. Blepharitis is the result of dysfunctional meibomian glands of the eyelids that result from vascular engorgement at the margins. There is no known cure for blepharitis, only palliative treatments such as warm compresses and eyelid massage. Oral doxycycline can be used to control blepharitis, but such medication has side effects such as skin sensitivity to the sun, gastritis, esophageal ulcer, and diarrhea. Steroidal eye drops have also been used to control the problem, but also have deleterious side effects such cataracts and glaucoma.

Trichiasis is a condition of misdirected eyelashes that grow towards the eye instead of away from it. Trichiasis can be a chronic source of foreign body sensation, tearing, and cornea trauma.

For the last decade, intense pulsed light (IPL) has been used in dermatology to treat vascular and pigmented lesions of the skin. A relatively recent review of IPL appears in Raulin, MD, Christian et al, *Lasers In Surgery And Medicine*, IPL Technology: A Review, 32:78-87 (2003). IPL systems utilize a source that emits pulsed polychromatic light in a broad wavelength spectrum of 515-1200 nm. Utilizing selected wavelengths can heat and eliminate target structures such as varicose veins or pigmented skin. Hemoglobin largely absorbs at a wavelength of approximately 580 nm, and brown structures such as melanin absorb in the range of about 400 to 750 nm. Filters are used to allow the optimal wavelength to penetrate the tissue, thereby essentially heating only the target structure to the desired degree that causes the structure to disappear. The pulse duration, typically in milliseconds, can also be adjusted so that it is lower than the thermal relaxation time of the targeted structure. This avoids damage to the adjacent tissue. The interval between pulses, also in milliseconds, can be adjusted as well. The delay allows heat to decrease in adjacent tissue, while heat is maintained in target tissue. IPL treatment has proven effective for the treatment of vascular lesions of the skin, including benign venous formations, telangiectasias, hemangiomas, and port-wine stains. Pigmented lesions of the skin, such as macules, nevi, and melasma also effectively respond to IPL.

The light for IPL treatments is typically generated in a relatively large console that may or may not be mobile. The treatment is applied via a bulky, handheld head that is adapted for the exchange of different filter-coated crystals that select for desired wavelengths. One example of such a device is the Vasculight™ Intense Pulsed Light and Laser by Lumenis. A smaller version of an IPL device is the Quadra Q4 Platinum Series by DermaMed USA, Inc. Because IPL was specifically designed for use in dermatology, the present head design and filter-coated crystals are not suitable for the ocular application of IPL treatments. Heads currently in use typically require the user to grasp a large handle with four fingers and thumb, similar to grasping portable electric devices like a drill or mixer, or even grasping the handle on a briefcase. This configuration does not allow for precise maneuvering and control of the head to treat small structures in the eye or eyelid. Such design also precludes use of the head with a slitlamp microscope, which would be needed to accurately apply IPL to ocular structures.

The filter-coated crystals used in dermatology are also not suitable for ocular application, because they are too large and would apply IPL treatment to other ocular structures not requiring treatment. The smallest crystal dimension currently appears to be 8 mm, which is considered small for skin treatments, but is too large for application in ocular surface and eyelid treatments. Moreover, the large size of IPL heads prevents the operator from maintaining a precise, constant distance from the target structure. Typically, in dermatological use, a cool gel is applied to the skin, the upper surface of which is a few millimeters above the skin. The end of the crystal in the head is then held at the top of the gel, preferably not contacting the skin. Because of the cumbersome nature of the head, and the lack of any guiding or measuring device at the end of the crystal, the crystal may momentarily touch the skin or may move a significant distance above the top of the gel. Experience provides operators with a steady hand and a better sense of distance, but for ocular use of IPL more precision would still be required.

In an effort to assess the dangers and difficulties of using presently available IPL equipment on ocular structures, the inventor used a Lumenis IPL™ Quantum SR to try to determine the intraocular effect from the IPL applied to the outside of the sclera. A bovine sclera, obtained from a slaughterhouse, was initially used for this purpose. The proximal side of the sclera was covered with a typical dermatological IPL gel. The IPL head was held as steadily as possible so that the end of the crystal just touched the gel, which had a thickness of approximately 3 millimeters. IPL was applied, and an electronic thermometer with a wire probe was used to determine the temperature of the distal side of the sclera. Numerous readings were taken. After each IPL application, the sclera was allowed to cool and a fresh coating of gel was applied to the sclera. The temperatures were inconsistent. The most apparent reason was the inability to hold the head steady while actuating the IPL.

Because of the cumbersome structure of IPL devices, the manufacturers conspicuously warn against use of the device in the area of the eye. Documented reports of injury to the eye from IPL make physicians and manufacturers hesitant to use IPL on the eye itself. For example, focal damage to the iris with distortion of the pupil occurred in treating a two-year old child's birthmark. Sutter, F. K., et al, *Dermatology Surgery* (January 2003), Ocular Complication Of PhotoDerm VL Therapy For Facial Port-Wine Stain, 29(1): 111-12. The paper concluded that such therapy could damage ocular tissues and that appropriate eye protection during the dermatological procedure was essential, even though the procedure did not involve the eye itself. Likewise, page 2-4 of the October 2002 Operator's Manual for the IPL™ Quantum SR by Lumenis states:

Intense pulsed light emission presents an eye hazard . . .

Make sure that the patient and all those present in the treatment room guard against accidental exposure to this emission either directly from the treatment head or indirectly from a reflecting surface.

Never look directly at the light beam coming from the treatment head, even when wearing Lumenis eyewear.

Never point the treatment head so that it discharges into free space.

Section 2.3, pages 2-6 and 2-7, of the Operator's Manual is entitled Optical Safety and lists additional precautions that should the manufacturer suggests for operators, patients, and those in the room during application IPL.

A recent article describes a single instance in which some success was achieved by using IPL for the treatment of dry eye. Toyos, MD, Rolando et al, Eye World (September 2005), Case Report: Dry-Eye Symptoms Improve With Intense Pulse Light Treatment, 73-74. Even in this instance, external stick-on IPL shields were applied to the patient's eye area, covering the entire eye.

After obtaining inconsistent temperature readings with the Quantum SR and the bovine sclera, it was determined that IPL temperature measurements should be taken while maintaining a constant and predetermined distance between the crystal tip and the sclera. The goal was to evaluate whether the inner sclera temperature would be below, at, or exceed 65-75° C., which is the temperature at which blood coagulates and blood vessels collapse. This knowledge is necessary because vital inner choroidal and retinal blood vessels are adjacent to the sclera wall. A microscope base was modified so that an eye could be placed on the surface where a slide is typically placed. Four threaded posts were placed around the perimeter of the slide surface. Nuts were used to adjust the height of a second flat platform with an opening in the center. In this manner, the distal end of a filter-coated crystal in the IPL head of the Quantum SR could be placed at a fixed distance above the sclera of an eye, with the IPL passing through the center opening of the second platform. The support apparatus was used with a fresh, cadaverous human eye to measure the temperature of the inner surface of the sclera after the application of IPL. The eye was obtained from an eye bank and stored in standard preservation media. Initially the eye was refrigerated and allowed to reach room temperature prior to the experiment.

In this experiment, the distance between the crystal tip and the outer surface of the sclera was fixed at 3 millimeters. A 590 nanometer filter was used, with two 7 millisecond pulses. The fluence, in joules/cm$^2$, was varied between 20 and 60, and the time delay $\Delta t$ between pulses was varied between 20 and 50 milliseconds. The skin type was set to I on the Fitzpatrick Skin Type scale. As with the bovine sclera, each reading was separated by minutes and preceded by the application of the cooled IPL cooling gel. To measure the temperature of the inner surface of the sclera, the end of the wire probe of the electronic thermometer was run through and to the tip of an 23 gauge needle. The needle was inserted into the sclera and passed through the vitreous cavity toward the opposite part of the eye globe until resistance from the underside of the sclera was felt on the needle tip. The wire tip of the electronic thermometer was then pushed through the hollow needle until inner eye wall resistance was felt against the wire tip. IPL treatments were applied to the outer sclera directly over the temperature probe. Prior to each electronic temperature reading, the wire probe was pushed back through the needle to ensure contact against the inner wall of the sclera.

The results of the second set of experiments were more encouraging than the first. The following temperatures of the inner surface of the sclera were measured.

| | Fluence in joules/cm$^2$ | | | | |
|---|---|---|---|---|---|
| | 20 | 30 | 40 | 50 | 60 |
| $\Delta t$ = 20 ms | 19.2° C. | 21.7° C. | 22.6° C. | 27.0° C. | 25.1° C. |
| $\Delta t$ = 20 ms | 20.1° C. | 20.2° C. | 23.3° C. | | |
| $\Delta t$ = 30 ms | 20.6° C. | | | | |
| $\Delta t$ = 40 ms | 20.3° C. | | | | |
| $\Delta t$ = 50 ms | 20.0° C. | | | | |

Two final readings were taken, one with a fluence of 20 and one with 60. $\Delta t$ was 20 ms. With the crystal tip 3 mm above the sclera, the temperature of the retina was taken at approximately 180° from the cornea. There was no measurable temperature change.

The preceding data suggest that with the proper equipment and technique, the convective and conductive heat generated by IPL in the vicinity of the eye can be dealt with safely, since the temperatures were not close to the 65-75° C. threshold for blood coagulation that would affect the choroidal and retinal vessels at the inner scleral wall. Likewise, the heat absorbed by the external target structure and then conducted to adjacent tissue should not cause problems. Further study can determine the pulse durations that will still be lower than the thermal relaxation time of target structures such as conjunctival blood vessels. This will insure that excess energy is not absorbed by the sclera, thus damaging adjacent tissue or interior structures. Similarly, further study can determine the pulse intervals necessary to achieve thermal damage in the target structure while permitting the sclera or eyelid and smaller vessels to cool after the first pulse.

As presently used, however, the intensity of the pulsed light has also discouraged the use of IPL in ocular treatments. IPL is typically generated in the visible spectrum, occasionally encompassing some of the near-infrared spectrum. As seen from the preceding discussion, heat absorbed by the sclera through selective photothermolysis is far less problematic than the energy of the pulsed visible light. Without precise IPL application and eye protection, the light can pass through the cornea, burning it and the interior ocular structures behind it.

IPL has potential usefulness for treating conjunctival blood vessels and the other problems discussed above. As seen in the preceding discussion, there is a need for an apparatus and method to permanently and non-invasively treat conjunctival blood vessels, brown nevi, yellow pinguecula, pigmented lesions and tumors, and similar problems. Likewise, there is a need to better and non-invasively treat blepharitis and trichiasis. There is also a need to develop IPL equipment and methods of using it so that IPL can be used safely on the sclera and the adjacent eyelids. This includes making the application of the IPL more precise and protecting the cornea and the interior of the eye from the visible light.

SUMMARY OF THE INVENTION

The present invention solves the problems discussed above, permitting non-invasive treatment of numerous ophthalmic maladies. For example, it can be used to eliminate superficial blood vessels of the conjunctiva that overlie the sclera. Similarly, it can treat superficial lesions of the conjunctiva, such as brown nevi, yellow pinguecula, and other pigmented structures that can be cosmetically unattractive. The present invention can also permanently treat blepharitis by eliminating the vascular engorgement and abnormal pilosebaceous structures of the eyelid margins. It can be used for removal of misdirected eyelashes to resolve trichiasis.

The present invention includes a handpiece for use in the IPL treatment of small ocular lesions. Conjunctival blood vessels are typically 0.5-2 mm in diameter and may be 10 mm in length. In order to treat such ocular structures, the handpiece design allows for ease of use at the slitlamp microscope where the patient is sitting upright. The handpiece design may take several forms, but the most common form allows the user to hold the handpiece like a pen or pencil between the thumb and index finger. The elongated handpiece head may be a solid or flexible. The length of the handpiece may vary. The cross-section may be cylinder shape or rectangular shape or any other shape known to those in the art.

The present invention includes an apparatus and method that use the application of IPL. The invention includes a handpiece for precise manipulation by two or three digits and a distance guide releasably attachable to the handpiece. In a preferred embodiment of the invention the distance guide includes side openings that permit the dissipation of the heat and light created by a crystal that is the optical source of the IPL. The crystal may also be releasably attachable to the handpiece. The handpiece can also include one of various means for cooling as described in more detail below, and it can also include controls or displays related to the amount of IPL.

A method of treating ocular and periocular problems with IPL is also described and claimed. The method includes the steps of determining an area of an eye or eyelid to be treated; determining the amount of IPL necessary to treat the problem; selecting a crystal; determining a preferred distance between the crystal tip and the area to be treated; selecting a distance guide; attaching the crystal and the distance guide to a handpiece, the handpiece being sized and configured for precise digital manipulation; setting a plurality of parameters to control the amount of IPL to be applied; placing an eye shield over the eye, the shield configured to cover a portion of the eyeball, including the entire cornea, while permitting access to the area to be treated; holding the handpiece so that the distance guide touches the area to be treated; and applying the IPL to the area to be treated.

BRIEF DESCRIPTION OF THE DRAWINGS

Below is a detailed description of the present invention that refers to the novel aspects of the invention, a variety of structural equivalents known by those of skill in the art, and in that context refers to the following figures.

DETAILED DESCRIPTION OF THE PREFERRED EMBODIMENTS

Figure 1:
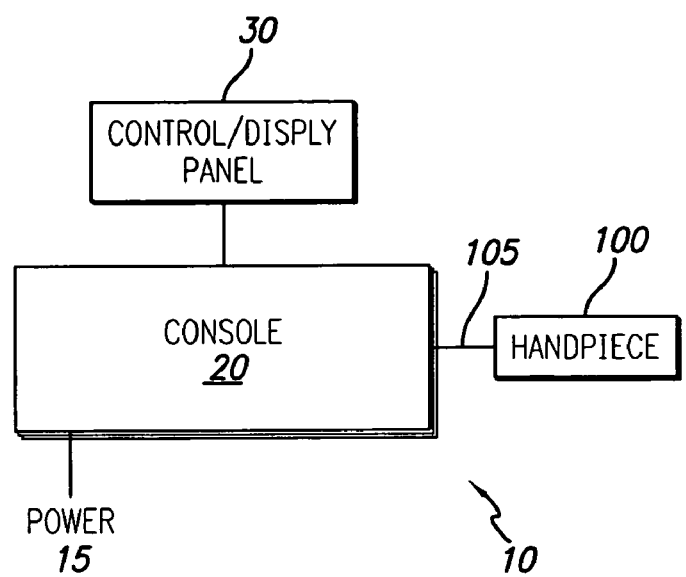
FIG. 1 is a schematic diagram of the present invention.

The present invention includes an apparatus 10 and method for applying IPL to the eye and eyelid to permanently but non-invasively treat problems such as those previously enumerated. FIG. 1 is a schematic diagram of the apparatus 10. A power source 15 and a control and display panel 30 connect to console 20. In FIG. 1, handpiece 100 also connects to the console and is used to directly apply IPL to a patient's eye. The physical arrangement of the parts of the invention 10 should not be limited to the one suggested in FIG. 1. As those of skill in the art understand, numerous ways exist to size and configure these parts. Such factors may be influenced or determined by cost, manufacturing considerations, and features that make the invention more appealing to the physicians who purchase it. For example, the control and display panel 30 can be a separate part mounted on console 20, or it can be an integral part of the console. The console itself can be fixed or movable. Alternatively, the console can be installed at a fixed location in the treatment room but removed from the chair or table occupied by the patient during treatment, while just the panel is fixed or movably located in the immediate vicinity of the treatment location. While the preferred embodiment of the invention 10 includes a single control and display panel 30, the invention should not be so limited. The control and display functions may be combined or separated.

The configuration and connection of the handpiece 100 can also be varied. It may, for example, be desirable to have some display or control features located directly on the handpiece 100. Likewise, any mechanical and electrical connections to obtain power from the console 20 for the handpiece 100 may come directly from the console 20 or may be routed through the panel 30. Thus, the handpiece 100 may be connected to either the console 20, the panel 30, or both. An actuation mechanism, such as a button (not shown), is preferably disposed on the handpiece. Alternatively, the actuation mechanism may be located other than on the handpiece for actuation by an assistant at the physician's oral instruction.

Figure 2:
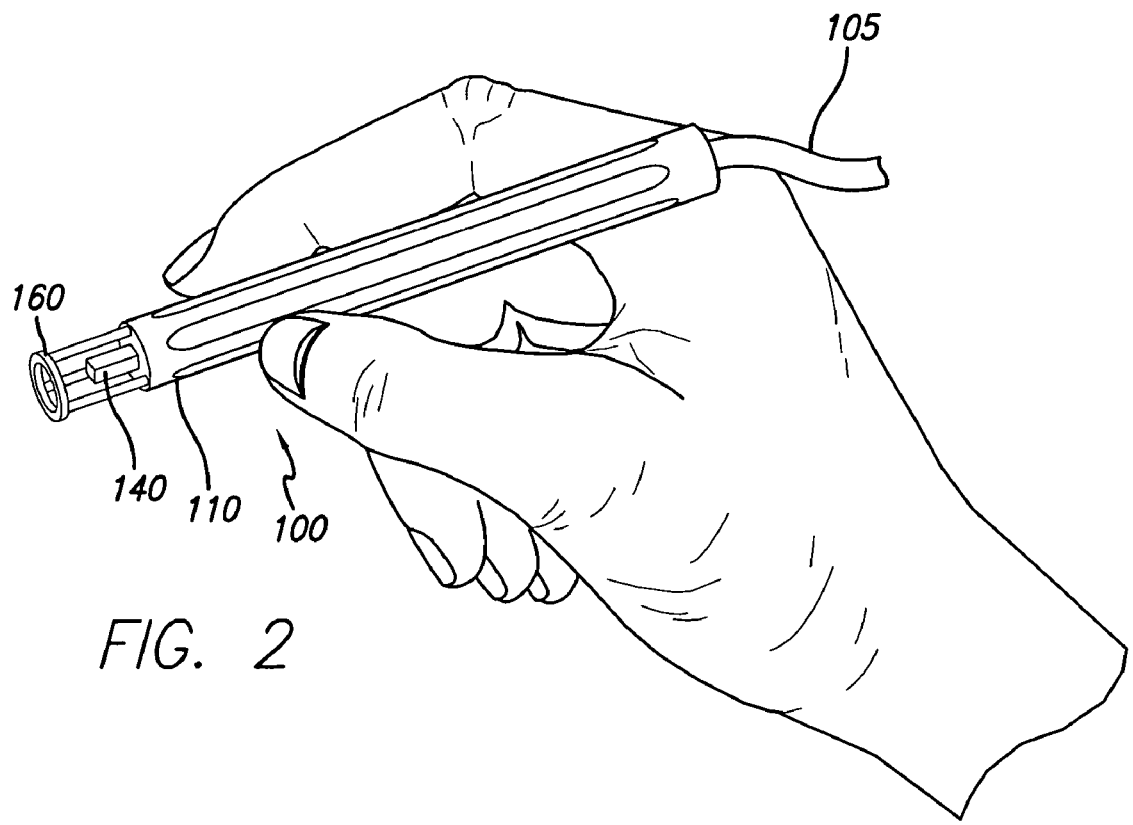
FIG. 2 is a perspective view of a preferred embodiment of the handpiece of the present invention.
Figure 3:
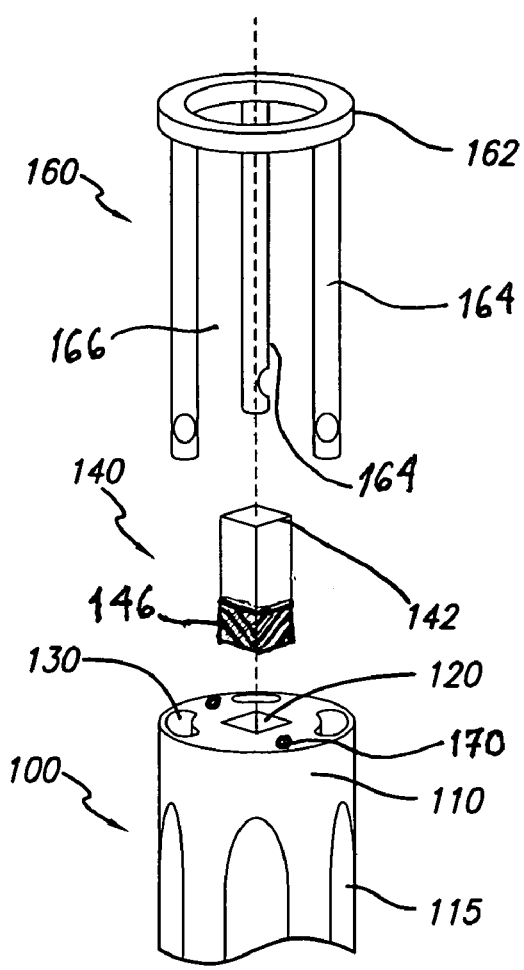
FIG. 3 is an exploded view of the handpiece of FIG. 2.

FIGS. 2 and 3 depict the basic arrangement of the handpiece 100. Grip or handle 110 is sized and configured so it can be held in a manner somewhat like holding a pencil, as depicted in FIG. 2. To improve a physician's control, the grip surface can be roughened or made of a grip-facilitating material (not shown); it can include shallow troughs 115; or, it can incorporate any one of numerous well-known techniques for enhancing the ability to grip a device by one's fingers. One end of grip 110 is connected to a power and control source, such as by connection 105. The other end of grip 110 has an opening 120 that is adapted to receive a crystal 140 through which the IPL is applied to the eye. The crystal, sometimes referred to as a crystal guide or light guide, is typically made from glass and filter-coated. In an embodiment where crystal 140 is removable, the proximal end of the crystal sits in a base portion 146, as seen in FIG. 3. Preferably, opening 120 in grip 110 is adapted so base portion 146 can be snapped securely into the grip 110. This embodiment permits the removal and replacement of varying size crystals while using a single grip 110 with a single size opening 120.

Distance guide 160 is also designed to snap into slots 130. When both the crystal 140 and distance guide 160 are secured in grip 110, it is desirable for the distal end 142 of crystal 140 to be approximately 3 millimeters from the eye when the ring-shaped distal end 162 of distance guide 160 is touching the eye or eyelid. The invention contemplates that the physician will have available of number of distance guides that will allow him to control the distance between the end of the optical guide and the area of the eye or eyelid to be treated. The distance guide may or may not have openings that permit the dissipation of light and heat from the optical guide. FIG. 3 depicts one embodiment of the distance guide, in which the guide 160 has three legs or members 164 separated by three side openings 166. In FIG. 3, the surface area of the side openings 166 at the outer circumference of the distance guide are substantially larger than the surface area of the outer surface of the distance guide members 166. Although FIG. 3 depicts the members as rods, the distance guide can, as discussed below, have virtually any practical configuration and is not limited to the embodiment depicted in FIG. 3.

The crystal is removable and selected for various sizes and lengths of ocular lesions to be treated. The largest cross-sectional dimension of the distal end of crystal 140 preferably ranges from 1 mm to 7 mm. The cross section may take any shape, such as a square, a rectangle, or a curved or polygonal shape, whichever may be most suitable for a specific application of IPL to the eye or eyelid. As with current IPL devices, the crystal may be coated to filter specific wavelengths. To diminish the amount of light flashing in the physician's or patient's eyes, a light-blocking coating may be applied to one or more of the vertical walls of the crystal while keeping the base of the filter clear for IPL treatment of the ocular structure.

Figure 6:
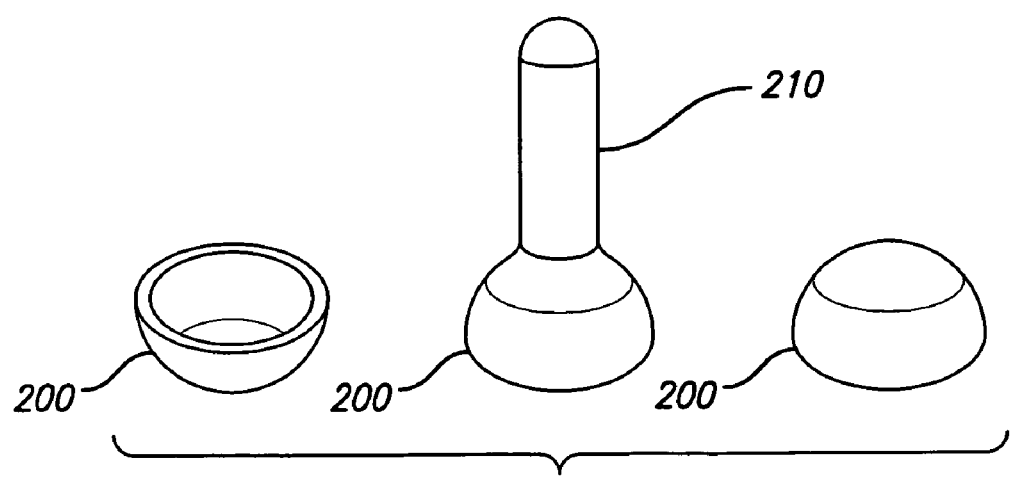
FIG. 6 is a perspective view of eye shields that are used during the application of IPL.

As noted earlier, ocular treatment with the present invention will require protection of the cornea from the IPL flashes. FIG. 6 depicts eye shield 200 and applicator 210. Similar shields have been used for surgery of the eyelids and orbital region of the face. These shields should be used for protecting the cornea during application of the IPL to the eye. In addition, the present invention contemplates eye shields that may be larger than a typical corneal shield, depending on the size and location of the lesion to be treated. This will protect portions of the sclera that do not require treatment from any unnecessary heat generated by the IPL. As long as the cornea is completely covered, the shield can be as large as necessary and located wherever necessary to additionally protect as much of the sclera as desired. Preferably the shield is made of medical grade plastic, to prevent absorption and conduction of any heat generated by the IPL.

Large IPL devices used in dermatology typically include mechanisms to cool the crystal. This prevents too much heat from raising skin temperature at the treatment site. Because the work in and around the eye will typically treat smaller structures than those encountered in dermatology, it is anticipated that less heat will be generated in the handpiece of the present invention. Therefore, it is contemplated that the handpiece 100 in FIGS. 2 and 3 will not have a cooling mechanism. If necessary, however, some form of cooling mechanism can be installed. For example, vents for air cooling could be placed in grip 110, or a small fan could be placed inside the grip. The chip cooling technology of laptops and personal computers can be adapted for such a function. Alternatively, connection 105 could include a flexible tube with a circulating fluid cooled and pumped by a very small chiller (not shown), which could be located inside console 20 or elsewhere. Those of skill in the art could adapt such technology from the dental arts, where for many years drills have been water-cooled to reduce the discomfort of drilling.

In addition to a crystal cooling arrangement, the grip 110 can also include the capability for applying a cooling spray directly to the treated area of the patient. FIG. 3 depicts small openings 170 in the distal end of grip 110 through which a cooling liquid could be sprayed. Here, too, other embodiments are also possible. For example, the spray could flow through the grip 110, members 164, and exit through openings (not shown) in ring 162. Alternatively, if the distance guide does not include a structure like the ring at the distal end 162 of distance guide 160, openings (not shown) at or near the ends of members 164 could emit a cooling spray.

Figure 4:
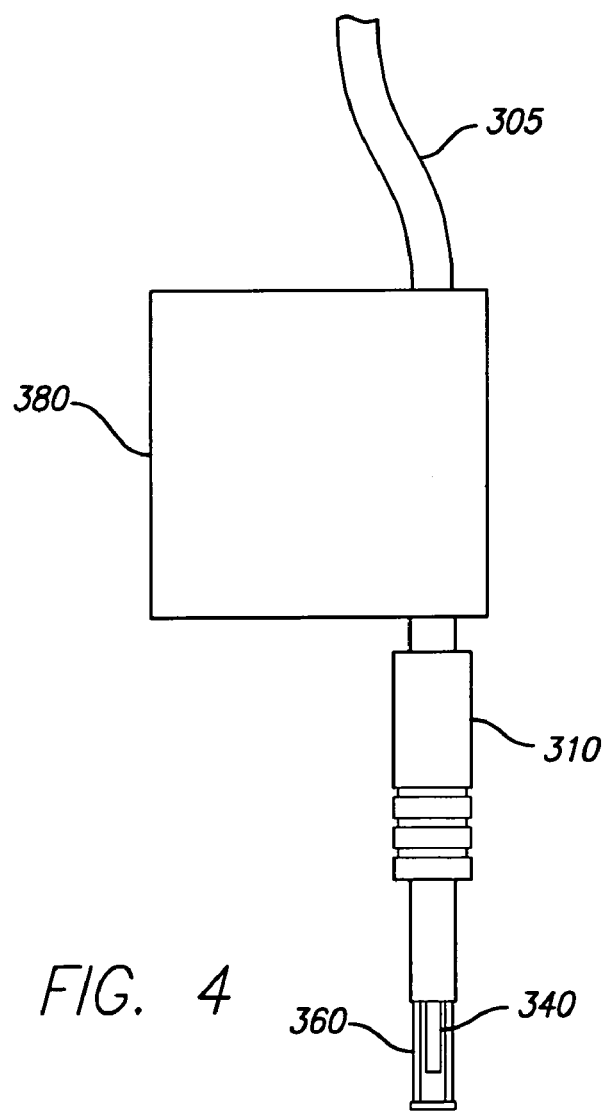
FIG. 4 is a perspective of a second embodiment of a handpiece for use with the present invention.
Figure 5:
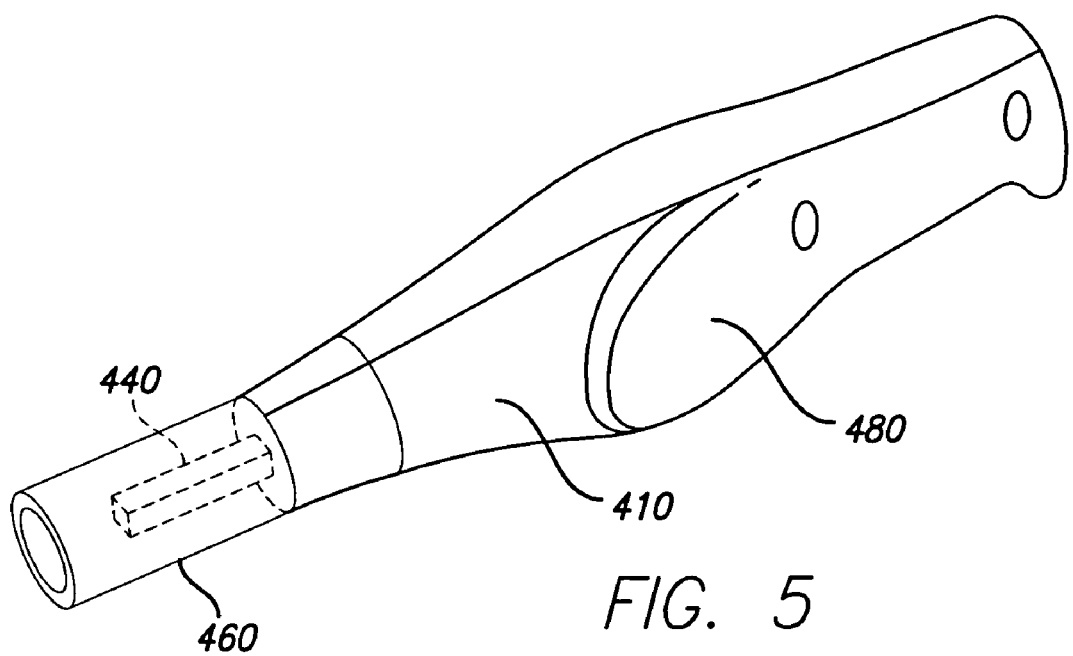
FIG. 5 is a perspective view of a third embodiment of a handpiece for use with the present invention.

FIG. 4 depicts another embodiment of the invention 300 that is capable of accommodating some form of cooling feature. Like the invention 100 in FIGS. 2 and 3, the embodiment in FIG. 4 depicts a connection 305 to a grip 310 that holds a crystal 340 and a distance gauge 360. The grip 310 includes an enclosure 380 disposed on the distal end of the grip 310. The enclosure 380 may contain a thermo-electric cooler or other mechanism to cool the crystal. FIG. 5 depicts an additional embodiment similar in function to that of FIG. 4. It includes a grip 410, connection 405, crystal 440, and distance guide 460. While grip 410 does not include a separate, distinctly identifiable enclosure like enclosure 380 of FIG. 4, the enclosure 480 of grip 410 is large enough to accommodate additional equipment for cooling.

The design of power, control, and display features of the present invention can be accomplished by those of skill in the art. The IPL settings will be adjustable. For example, parameters such as pulse duration may vary between 0.5-100 milliseconds, and parameters such as fluence between 3-150 joules/cm$^2$. The pulse delay parameter may have a range from 1 to 300 milliseconds. In most instances, the settings will likely be at the lower end of these ranges. Wavelength filters will be determined by the type of treatment necessary. While hemoglobin absorbs primarily at about 580 nm, the spectral range of melanin absorption covers 400-750 nm. The preferred settings for different pathologies in different patients will be determined during commercial development, clinical trials, and by practical experience. Adjustment of the IPL parameters or multiple treatments may be required for full resolution of a targeted structure.

Those of skill in the art will understand that changes may be made to the present invention without departing from its spirit or from the scope of the claims. For example, the preferred embodiment of the invention uses removable and replaceable crystals and distance guides that are separate structures. The invention should not be so limited. For example, individual handpieces could be manufactured with permanently installed crystals, or ones that could only be removed by opening the grip, so that the physician would choose different grips if he wanted a differently shaped guide or one with a different wave frequency filter coating. Alternatively, the crystal and distance guide could be manufactured as a single integral unit that could be releasably mounted in the grip. In addition, the invention can be adapted so that a variety of releasably attachable distance guides can maintain a particular crystal tip at varying distances from the eye. Nor should the present invention necessarily be limited to the treatment of the eye and eyelid. It can also be used when more precise dermatological applications are called for.

Similarly, the handpiece in FIG. 4 depicts an enclosure 380 at the distal end of grip 310, which can accommodate power or cooling mechanisms. Such an enclosure could be disposed between the console and/or control panel and not be directly a part of the grip. Or such an enclosure could include the components necessary to provide some or all of the control and display functions of the present invention. Another variation in the present invention can be seen in distance guide 440, in which the sides are completely enclosed by a solid wall. In an yet another embodiment, the walls of the distance guide can have openings of varying size to let light escape to avoid overheating the crystal or the sclera. For example, FIG. 3 depicts three equally spaced legs or rods 164 with a ring at the distal end 162 that function as the distance guide. Alternatively, the distance guide could simply be one or more legs, without the ring at the distal end 162. Similarly, the distance guide could comprise one or more spaced segments of the cylindrical shell depicted in FIG. 5. Ultimately, configuration of the distance guide is limited only by the practicalities of visual and physical access to the area being treated.

Some existing technology could be added to the present invention to further minimize the potential for heat damage. As noted earlier, a mechanism for applying a cooling spray to the skin could be incorporated into the handpiece, as has been done with more sophisticated and larger units used in dermatological applications. Various embodiments could be used, such as replacing openings 170 with small nozzles. Controls could be added either directly to the handpiece or at a remote location to control the timing and amount of the cooling spray. Thus, the scope of the invention should be understood in the context of the specification and as it is defined in the following claims.

What is claimed is:

1. A method for precisely and non-invasively using intense pulsed light (IPL) to treat eye-related problems such as small blood vessels, small lesions and tumors, small dermatological stains and pigmented structures, ingrown hairs, and the like, comprising the steps of:

determining an area of the eye or the eyelid to be treated;
determining an amount of IPL necessary to treat the problem;
selecting a crystal;
determining a preferred distance between the crystal and the area to be treated;
selecting a distance guide;
attaching the crystal and the distance guide to a handpiece, the handpiece being sized and configured for precise digital manipulation by an operator's fingers to apply IPL to non-corneal portions of the eye;
setting a plurality of parameters to control the amount of IPL to be applied;
placing an eye shield over the eye, the shield configured to cover a portion of the eyeball, including the entire cornea, while permitting access to the area to be treated by the IPL;
holding the handpiece so that the distance guide touches the area to be treated; and
applying the IPL to the area to be treated.

2. The method of claim 1, wherein the step of attaching the crystal and the distance guide to the handpiece includes attaching a single, releasably attachable unit comprising both the crystal and the distance guide.

3. The method of claim 1, wherein the step of determining a preferred distance and selecting a distance guide includes selecting a distance guide comprising a solid tube with openings.

4. The method of claim 3, wherein the step of attaching the crystal and the distance guide to a handpiece includes a handpiece with at least one of a control and display of a parameter related to the amount of the IPL.

5. The method of claim 3, wherein the step of attaching the crystal and the distance guide to a handpiece includes a handpiece adapted to contains means for cooling the crystal.

* * * * *